(12) United States Patent
Takahashi et al.

(10) Patent No.: US 7,193,087 B2
(45) Date of Patent: Mar. 20, 2007

(54) 4-AMINOPYRIDINIUM COMPOUND

(75) Inventors: Makoto Takahashi, Kanagawa (JP); Shinichi Morishima, Kanagawa (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 216 days.

(21) Appl. No.: 11/089,507

(22) Filed: Mar. 25, 2005

(65) Prior Publication Data

US 2005/0211954 A1    Sep. 29, 2005

(30) Foreign Application Priority Data

Mar. 26, 2004    (JP)    ............................. 2004-092466

(51) Int. Cl.
  *C07D 213/74*    (2006.01)
  *C07D 213/20*    (2006.01)
  *C07D 213/38*    (2006.01)
  *C09K 19/56*    (2006.01)

(52) U.S. Cl. .................................. 546/347; 252/299.4

(58) Field of Classification Search ........... 252/299.01, 252/299.4; 546/264, 347
See application file for complete search history.

(56) References Cited

U.S. PATENT DOCUMENTS 4,978,659 A  *  12/1990  DiNinno et al. ............... 514/80
6,107,494 A  *   8/2000  Lee et al. ...................... 549/9

FOREIGN PATENT DOCUMENTS

| JP | 2002-37776 | * | 2/2002 |
| JP | 2002-37777 | * | 2/2002 |
| JP | 2002-38158 | * | 2/2002 |

OTHER PUBLICATIONS

English translation by computer for JP 2002-37777, http://www4.ipdl.ncipi.go.jp/Tokujitu/PAJdetail.ipdl?N0000=60&N0120=01&N2001=2&N3001=2002-037777.*
English translation by computer for JP 2002-37776, http://www4.ipdl.ncipi.go.jp/Tokujitu/PAJdetail.ipdl?N0000=60&N0120=01&N2001=2&N3001=2002-037776.*
English translation by computer JP 2002-38158, http://www4.ipdl.ncipi.go.jp/Tokujitu/PAJdetail.ipdl?N0000=60&N0120=01&N2001=2&N3001=2002-038158.*

* cited by examiner

Primary Examiner—Shean C. Wu
(74) Attorney, Agent, or Firm—Buchanan Ingersoll & Rooney PC

(57) ABSTRACT

A 4-aminopyridinium compound is represented by the formula (I) or (II).

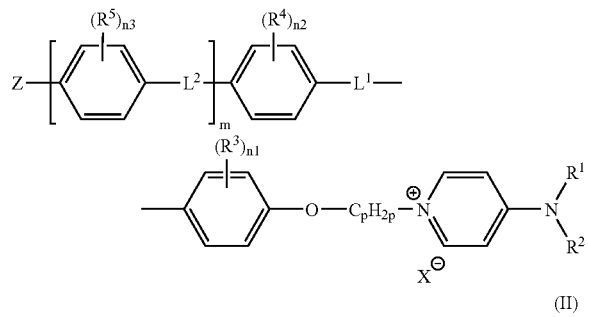

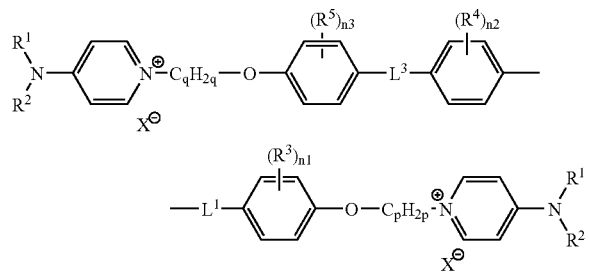

in which each of $L^1$ and $L^3$ is —O—CO—, —CO—O—, —C≡C—, —CH=CH—, —CH=N—, —N=CH— or —N=N—; $L^2$ is a single bond, —O—CO—, —CO—O—, —C≡C—, —CH=CH—, —CH=N—, —N=CH— or —N=N—; m is 0 or 1; each of p and q is 1 to 10; each of $R^1$ and $R^2$ is an alkyl group or $R^1$ and $R^2$ are combined to form a ring; Z is cyano, an alkyl group, an alkoxy group, an acylalkyl group, an acylalkoxy group, an acyloxyalkyl group or an acyloxyalkoxy group; each of $R^3$, $R^4$ and $R^5$ is a halogen atom; each of n1, n2 and n3 is 0 or 1; and X is an anion.

18 Claims, No Drawings

4-AMINOPYRIDINIUM COMPOUND

FIELD OF THE INVENTION

The present invention relates a compound having a pyridinium ring to which a dialkylamino group or a nitrogen-containing saturated heterocyclic group is attached as a substituent group at 4-position. The invention also relates a 4-aminopyridinium compound capable of controlling a tilt (or inclined) angle of aligned liquid crystal molecules.

BACKGROUND OF THE INVENTION

A liquid crystal compound can form a liquid crystal layer, which behaves as both liquid having fluidity and crystal consisting of regularly aligned molecules under some conditions. The liquid crystal compound is widely used in various liquid crystal devises such as a liquid crystal display. In producing any devises, it is important to control alignment (orientation) of the liquid crystal molecules. Examples of the alignment include homeotropic alignment, homogeneous alignment, tilt alignment, hybrid alignment, twisted alignment, planar alignment and focal conic alignment. The alignments are described in "Basics and Application of Liquid Crystal (written in Japanese)", Kogyo Chosakai Publishing Inc., 1991.

Alignment of a liquid crystal compound generally depends on alignment technique and a character of the liquid crystal compound. The alignment technique can be applied to a surface of substrate in a conventional manner described in "Basics and Application of Liquid Crystal (written in Japanese)", Kogyo Chosakai Publishing Inc., 1991). Various alignment techniques have been proposed. For example, Appl. Phys. Lett., 27(1975), pp. 268; ibid., 29(1976), pp. 67; and ibid., 22(1973), pp. 111 disclose a process for chemically adsorbing an aligning promoter such as chromium carboxylate complex or organosilane on a surface of substrate to align the liquid crystal molecules vertically or horizontally. Ouyo-Butsuri (written in Japanese), 43(1974), pp. 18; Phys. Rev. Lett., 25(1976), pp. 67 discloses a process of adsorbing an aligning promoter physically on a substrate surface to align the liquid crystal molecules vertically or horizontally. Appl. Phys. Lett., 24(1974), pp. 297 discloses a process of polymerizing and adsorbing a substance of low molecular weight on a substrate surface by plasma discharge to align the liquid crystal molecules vertically or horizontally. J. Appl. Phys., 47(1976), pp. 1,270 discloses a process of polymerizing and adsorbing a substance of high molecular weight on a substrate surface by an electric field of high voltage to align the liquid crystal molecules vertically or horizontally. Appl. Phys. Lett., 25(1974), pp. 479 discloses an oblique deposition method to cause oblique and homogeneous alignment. In the oblique deposition method, oxide such as silicon oxide is obliquely deposited on a substrate. A vertically aligning promoter can be used in the oblique deposition method to align molecules vertically and obliquely. Summaries of 6th Forum on Liquid Crystal (in Japanese), (1980), pp. 96 discloses a process of depositing an oxide such as silicon oxide obliquely while rotating a substrate to cause vertical and oblique alignment.

As described above, various aligning techniques have been proposed. Further, a process of obliquely aligning liquid crystal molecules has been proposed. However, it is difficult to control a tilt angle sufficiently according to the techniques. Accordingly, an agent capable of controlling the tilt angle has been desired. The agent should have a function of controlling the tilt angle in alignment of liquid crystal molecules easily.

Each of International Publication Nos. 98/40375, 97/33882 and U.S. Pat. No. 4,978,659 discloses a 1-azabicyclo[3.2.0]heptane derivative having dimethylamino-pyridinium group at a terminal of side chain. The 1-azabicyclo[3.2.0]heptane derivative is proposed for medical or pharmaceutical use.

Each of Japanese Patent Provisional Publication Nos. 2002-37776, 2002-37777, 2002-38158, 2002-62533 and 2002-62531 discloses an aminopyridinium derivative substituted with an aliphatic group. The publications also disclose a method of using the derivative to control a tilt angle in alignment of liquid crystal molecules.

SUMMERY OF THE INVENTION

It is an object of the present invention to provide a compound capable of controlling a tilt angle in alignment of liquid crystal molecules. The compound preferably has such a function that a small amount of the compound can easily control the tilt angle.

The object of the invention is achieved by the compound defined in (1) to (17)

(1) A 4-aminopyridinium compound represented by the following formula (I):

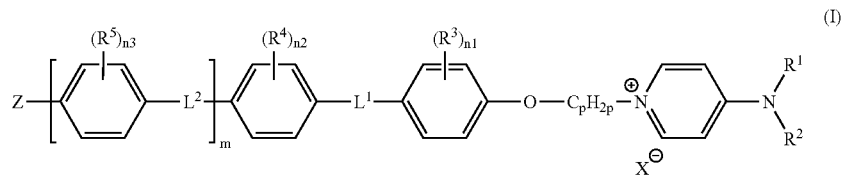

in which $L^1$ is —O—CO—, —CO—O—, —C≡C—, —CH=CH—, —CH=N—, —N=CH— or —N=N—; $L^2$ is a single bond, —O—CO—, —CO—O—, —C≡C—, —CH=CH—, —CH=N—, —N=CH— or —N=N—; m is 0 or 1; p is an integer of 1 to 10; each of $R^1$ and $R^2$ is independently an alkyl group having 1 to 8 carbon atoms, or otherwise $R^1$ and $R^2$ are combined to form a nitrogen-containing saturated ring; Z is cyano, an alkyl group having 1 to 12 carbon atoms, an alkoxy group having 1 to 12 carbon atoms, an acylalkyl group having 3 to 24 carbon atoms, an acylalkoxy group having 3 to 24 carbon atoms, an acyloxyalkyl group having 3 to 24 carbon atoms or an acyloxyalkoxy group having 3 to 24 carbon atoms; each of $R^3$, $R^4$ and $R^5$ is independently a halogen atom; each of n1, n2 and n3 is independently 0 or 1; and X is an anion.

(2) The compound of (1), wherein $L^1$ in the formula (I) is —O—CO—, —C≡C—, —CH=CH—, —CH=N— or —N=N—.

(3) The compound of (1), wherein $L^2$ in the formula (I) is a single bond, —CO—O—, —C≡C—, —CH=CH—, —N=CH— or —N=N—.

(4) The compound of (1), wherein m in the formula (I) is 1.

(5) The compound of (1), wherein $C_pH_{2p}$ in the formula (I) is an alkylene group of a straight chain represented by $(CH_2)_p$.

(6) The compound of (1), wherein each of $R^1$ and $R^2$ in the formula (I) is independently an alkyl group having 1 to 6 carbon atoms.

(7) The compound of (1), wherein each of n1, n2 and n3 in the formula (I) is independently 0.

(8) The compound of (4), wherein Z in the formula (I) is cyano, an alkyl group having 1 to 10 carbon atoms or an alkoxy group having 1 to 10 carbon atoms.

(9) The compound of (1), wherein m in the formula (I) is 0, and Z in the formula (I) is an alkyl group having 7 to 12 carbon atoms, an alkoxy group having 7 to 12 carbon atoms, an acylalkyl group having 7 to 12 carbon atoms, an acylalkoxy group having 7 to 12 carbon atoms, an acyloxyalkyl group having 7 to 12 carbon atoms or an acyloxyalkoxy group having 7 to 12 carbon atoms.

(10) The compound of (1), wherein X in the formula (I) is a halide ion or a sulfonate ion.

(11) A 4-aminopyridinium compound represented by the following formula (II):

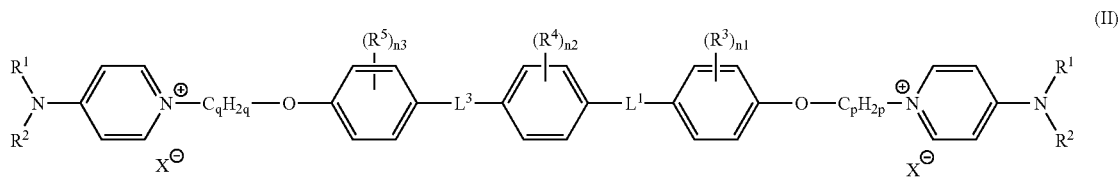

in which each of $L^1$ and $L^3$ is independently —O—CO—, —CO—O—, —C≡C—, —CH=CH—, —CH=N—, —N=CH— or —N=N—; each of p and q is independently an integer of 1 to 10; each of $R^1$ and $R^2$ is independently an alkyl group having 1 to 8 carbon atoms, or otherwise $R^1$ and $R^2$ are combined to form a nitrogen-containing saturated ring; each of $R^3$, $R^4$ and $R^5$ is independently a halogen atom; each of n1, n2 and n3 is independently 0 or 1; and X is an anion.

(12) The compound of (11), wherein $L^1$ in the formula (II) is —O—CO—, —C≡C—, —CH=CH—, —CH=N— or —N=N—.

(13) The compound of (11), wherein $L^3$ in the formula (II) is —CO—O—, —C≡C—, —CH=CH—, —N=CH— or —N=N—.

(14) The compound of (11), wherein $C_pH_{2p}$ in the formula (II) is independently an alkylene group of a straight chain represented by $(CH_2)_p$.

(15) The compound of (11), wherein $C_qH_{2q}$ in the formula (II) is independently an alkylene group of a straight chain represented by $(CH_2)_q$.

(16) The compound of (11), wherein each of $R^1$ and $R^2$ in the formula (II) is independently an alkyl group having 1 to 6 carbon atoms.

(17) The compound of (11), wherein each of n1, n2 and n3 in the formula (II) is independently 0.

(18) The compound of (11), wherein X in the formula (II) is a halide ion or a sulfonate ion.

The applicants have been searched for a compound capable of controlling a tilt angle, and finally found that the 4-aminopyridinium compound represented by the formula (I) or (II). The 4-aminopyridinium compound represented by the formula (I) or (II) shows an excellent function of controlling the tilt angle in alignment of liquid crystal molecules. Therefore, the tilt angle can easily be controlled by using a small amount of the 4-aminopyridinium compound.

DETAILED DESCRIPTION OF THE INVENTION

The 4-aminopyridinium compound is represented by the formula (I) or (II).

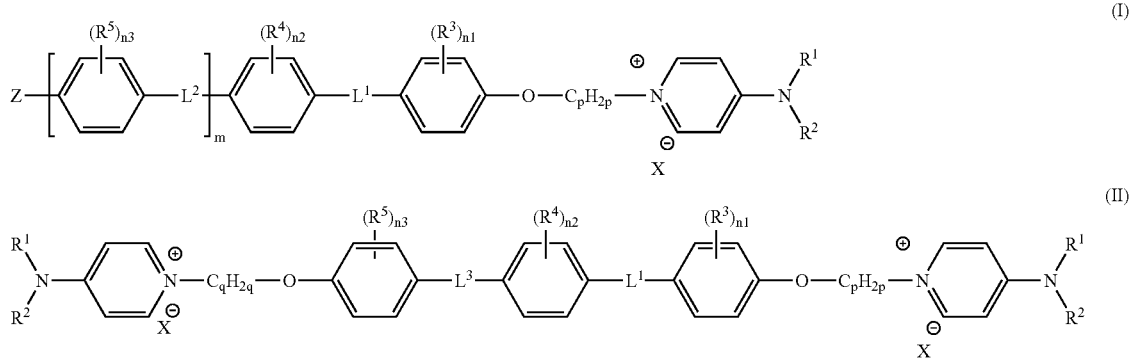

In the formulas (I) and (II), each of $L^1$ and $L^3$ is independently —O—CO—, —CO—O—, —C≡C—, —CH=CH—, —CH=N—, —N=CH— or —N=N—.

The group $L^1$ is preferably —O—CO—, —C≡C—, —CH=CH—, —CH=N— or —N=N—.

The group $L^3$ is preferably —CO—O—, —C≡C—, —CH=CH—, —N=CH— or —N=N—.

In the formula (I), $L^2$ is a single bond, —O—CO—, —CO—O—, —C≡C—, —CH=CH—, —CH=N—, —N=CH— or —N=N—.

The group $L^2$ is preferably a single bond, —CO—O—, —C≡C—, —CH=CH—, —N=CH— or —N=N—.

In the formula (I), m is 0 or 1, and preferably is 1.

In the formulas (I) and (II), each of p and q is independently an integer of 1 to 10. Each of $C_pH_{2p}$ and $C_qH_{2q}$ means an alkylene group having a chain structure, which can be branched. Each of $C_pH_{2p}$ and $C_qH_{2q}$ preferably is an alkylene group having a straight chain structure. In other words, $C_pH_{2p}$ is preferably represented by $(CH_2)_p$, and $C_qH_{2q}$ is preferably represented by $(CH_2)_q$.

In the formulas (I) and (II), each of $R^1$ and $R^2$ is independently an alkyl group having 1 to 8 carbon atoms, or otherwise $R^1$ and $R^2$ are combined to form a nitrogen-containing saturated ring.

The alkyl group can have a cyclic structure or a branched chain structure. The alkyl group preferably has 1 to 6 carbon atoms.

The nitrogen-containing saturated ring formed by the combined $R^1$ and $R^2$ is preferably a 5-membered ring (e.g., pyrrolidine ring) or a 6-membered ring (e.g., piperidine ring).

In the formula (I), Z is cyano, an alkyl group having 1 to 12 carbon atoms, an alkoxy group having 1 to 12 carbon atoms, an acylalkyl group having 3 to 24 carbon atoms, an acylalkoxy group having 3 to 24 carbon atoms, an acyloxyalkyl group having 3 to 24 carbon atoms or an acyloxyalkoxy group having 3 to 24 carbon atoms. The alkyl moiety of the acylalkyl group and the acyloxyalkyl group and the alkoxy group of the acylalkoxy group and the acyloxyalkoxy group preferably have 1 to 12 carbon atoms. The acyl moiety of the acylalkyl group and the acylalkoxy group and the acyloxy moiety of the acyloxyalkyl group and the acyloxyalkoxy group preferably have 2 to 12 carbon atoms.

In the case where m is 1, Z is preferably cyano, an alkyl group having 1 to 10 carbon atoms or an alkoxy group having 1 to 10 carbon atoms.

In the case where m is 0, Z is preferably an alkyl group having 7 to 12 carbon atoms, an alkoxy group having 7 to 12 carbon atoms, an acylalkyl group having 7 to 12 carbon atoms, an acylalkoxy group having 7 to 12 carbon atoms, an acyloxyalkyl group having 7 to 12 carbon atoms or an acyloxyalkoxy group having 7 to 12 carbon atoms.

The acyl group is represented by —CO—R. The acyloxy group is represented by —O—CO—R. R is an aliphatic group (an alkyl group, a substituted alkyl group, an alkenyl group, a substituted alkenyl group, an alkynyl group, a substituted alkynyl group) or an aromatic group (an aryl group, a substituted aryl group). R is preferably an aliphatic group, and more preferably an alkyl group or an alkenyl group.

In the formulas (I) and (II), each of $R^3$, $R^4$ and $R^5$ is independently a halogen atom (F, Cl, Br, I).

In the formulas (I) and (II), each of n1, n2 and n3 is independently 0 or 1, and preferably 0.

In the formulas (I) and (II), X is an anion, and preferably a monovalent anion. Examples of the anion include a halide ion (fluoride ion, chloride ion, bromide ion, iodide ion) and a sulfonate ion (e.g., methanesulfonate ion, p-toluenesulfonate ion, benzenesulfonate ion).

Examples of the 4-aminopyridinium compounds represented by the formula (I) or (II) are shown below.

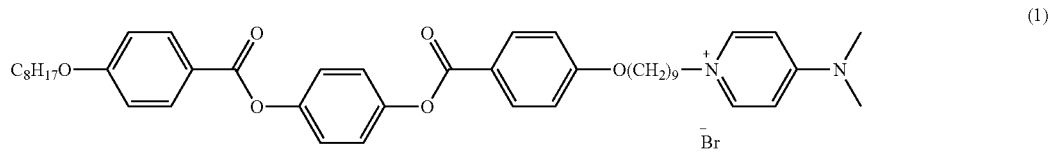

(1)

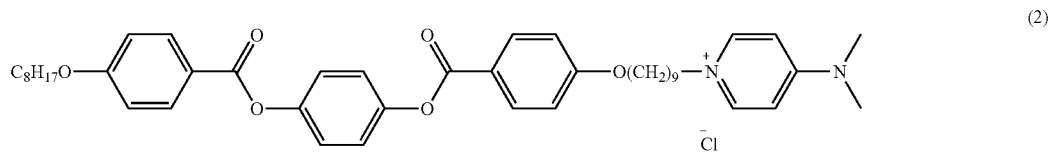

(2)

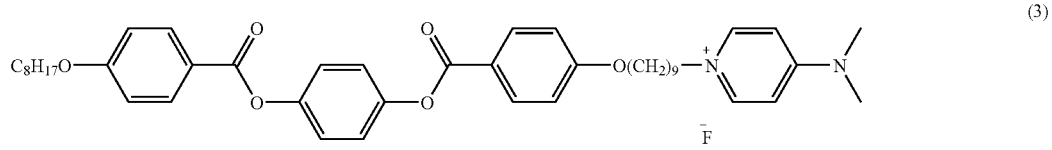

(3)

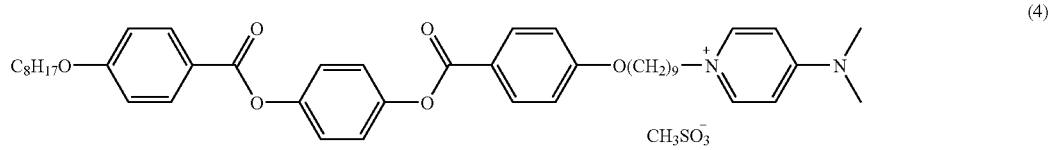

(4)

-continued
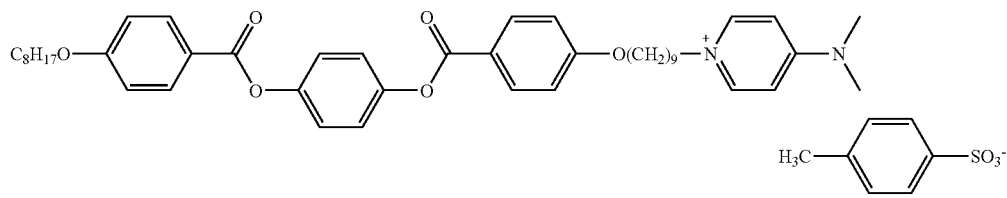
(5)
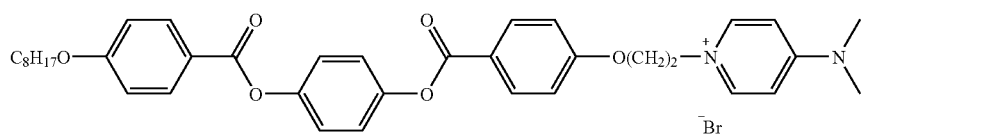
(6)
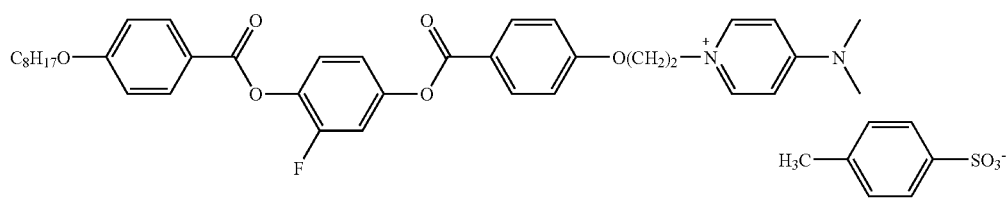
(7)
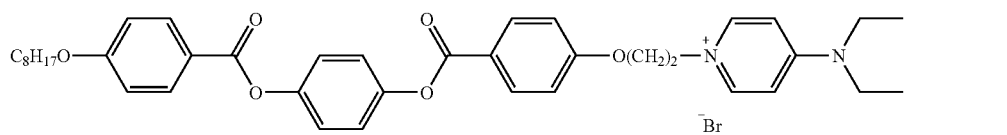
(8)
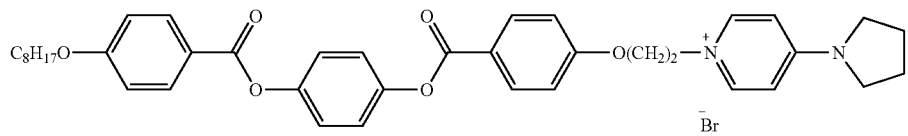
(9)
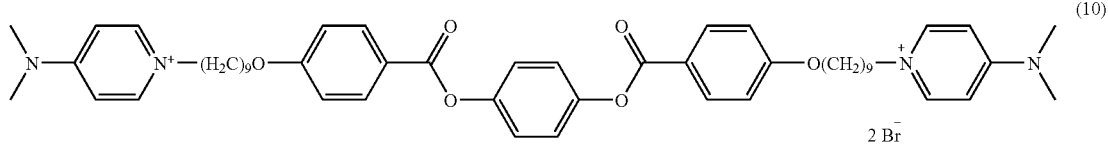
(10)
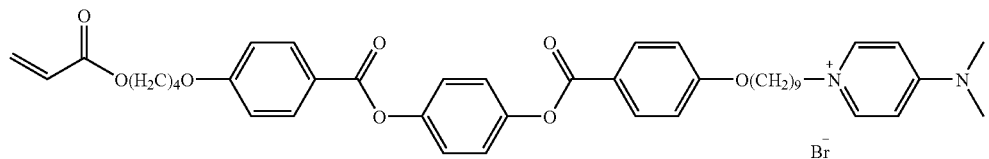
(11)
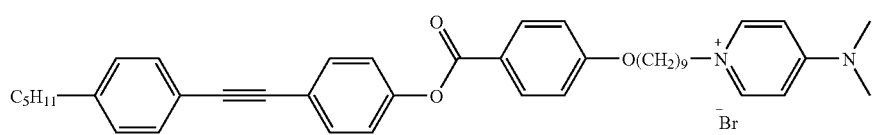
(12)
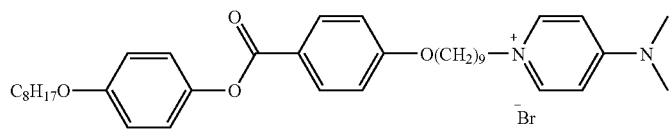
(13)
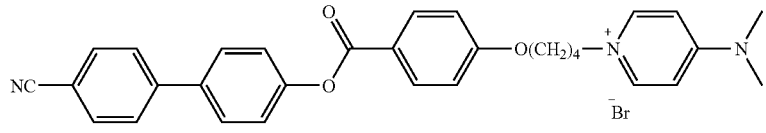
(14)

-continued

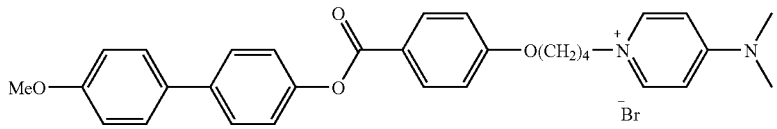
(15)

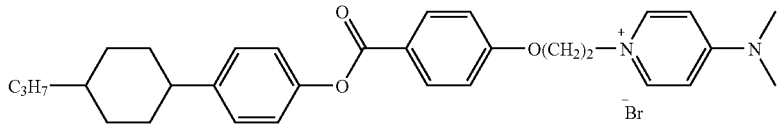
(16)

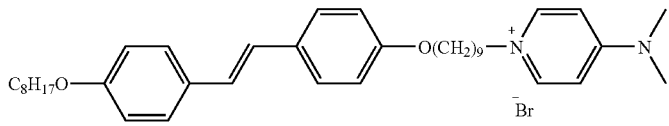
(17)

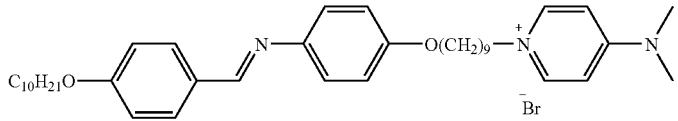
(18)

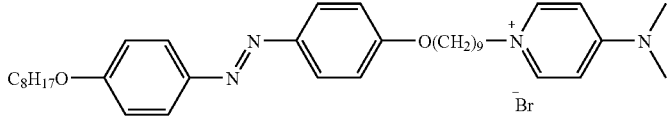
(19)

The compound of the formula (I) or (II) can be synthesized, for example, in the following manner.

A compound represented by the formula (III) is dissolved in an organic solvent.

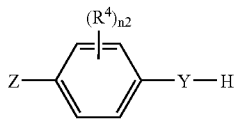
(III)

In the formula (III), Z, $R^4$ and n2 are the same as those defined in the formula (I).

In the formula (III), Y is oxygen, sulfur, imino (—NH—) or a substituted imino (—NR—, in which R is an alkyl group having 1 to 5 carbon atoms).

Examples of the organic solvents include an ester (e.g., tetrahydrofuran), an amide (e.g., dimethylformamide, N,N-dimethylacetamide), a halogenated hydrocarbon (e.g., dichloromethane), an ester (e.g., ethyl acetate), ketones (e.g., acetone) and a nitrile (e.g., acetonitrile).

A compound represented by the formula (IV) is reacted with the compound of the formula (III) in the presence of a base to prepare a compound represented by the formula (V).

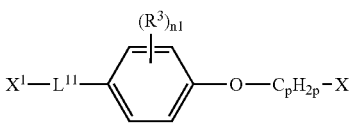
(IV)

In the formula (IV), $R^3$, n1 and p are the same as those defined in the formula (I).

In the formula (IV), $L^{11}$ is a precursor of $L^1$ in the formula (I).

In the formula (IV), $X^1$ is a releasing group.

In the formula (IV), X is a releasing group to be released to form the anion of X in the formula (I).

The base is preferably a tertiary amine (e.g., triethylamine, ethyldiisopropylamine).

A catalyst (e.g., 4-dimethylaminopyridine) is preferably used to accelerate a rate of reaction.

The reaction temperature is usually in the range of −20° C. to a boiling point of a solvent, and preferably in the range of 0 to 30° C.

The reaction time is preferably 10 minutes to 3 days, and more preferably 1 hour to 1 day.

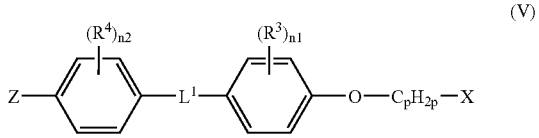

(V)

In the formula (V), $R^3$, $R^4$, n1, n2, p and Z are the same as those defined in the formula (I).

In the formula (V), X is a releasing group to be released to form the anion of X in the formula (I).

The compound of the formula (V) is reacted in an organic solvent with the compound represented by the formula (VI) to synthesize the compound of the formula (I) wherein m is 0.

(VI)

In the formula (VI), $R^1$ and $R^2$ are the same as those defined in the formula (I).

Examples of the organic solvents include a hydrocarbon (e.g., toluene), an ether (e.g., tetrahydrofuran), an amide (e.g., dimethylformamide, N,N-dimethylacetamide), a halogenated hydrocarbon (e.g., dichloromethane, chloroform), an ester (e.g., ethyl acetate), a ketone (e.g., acetone, 2-butanone) and a nitrile (e.g., acetonitrile).

The reaction temperature is usually in the range of −20° C. to the boiling point of the solvent.

The reaction mixture is preferably refluxed to promote the reaction.

The reaction time is preferably 10 minutes to 3 days, more preferably 1 hour to 1 day.

The above-described procedures can be conducted except that Z in the formula (III) is replaced with a functional group represented by the formula (VII) to synthesize a compound represented by the formula (I) wherein m is 1.

(VII)

In the formula (VII), $L^2$, $R^5$, n3 and Z are the same as those defined in the formula (I).

The above-described procedures can be conducted except that Z in the formula (III) is replaced with a functional group represented by the formula (VIII) to synthesize a compound represented by the formula (II).

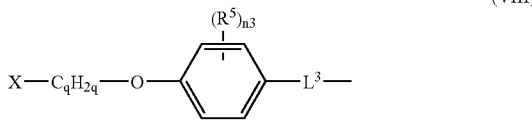

(VIII)

In the formula (VIII), $L^3$, $R^5$, n3, q and X are the same as those defined in the formula (II).

A compound having a precursor group or a protected group of Z in place of Z can also be used. The precursor group or the protected group can be converted to Z in a synthesizing reaction.

If a compound represented by the formula (IX) is easily available, the compound represented by the formulas (IX) can be reacted with a compound represented by the formula (X) in an organic solvent in the presence of a base. The compound of the formula (X) is preferably used in an excess amount, and more preferably in an amount of 1.5 equivalent or more.

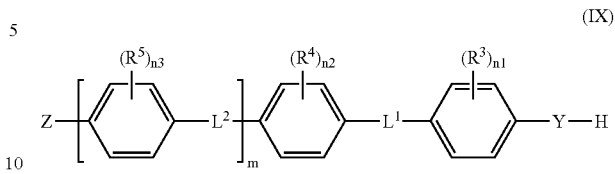

(IX)

In the formula (IX), $R^3$, $R^4$, $R^5$, $L^1$, $L^2$, m, n1, n2, n3 and Z are the same as those defined in the formula (I).

In the formula (IX), Y is oxygen, sulfur, imino (—NH—) or a substituted imino (—NR—, in which R is an alkyl group having 1 to 5 carbon atoms).

(X)

In the formula (X), p and X are the same as those defined in the formula (I).

Examples of the organic solvents include an ether (e.g., tetrahydrofuran), an amide (e.g., dimethylformamide, N,N-dimethylacetamide), a halogenated hydrocarbon (e.g., dichloromethane), an ester (e.g., ethyl acetate), ketones (e.g., acetone) and a nitrile (e.g., acetonitrile).

Examples of the bases include a carbonate (e.g., potassium carbonate) and a tertiary amine (e.g., triethylamine).

The reaction temperature is usually in the range of −20° C. to the boiling point of the solvent.

The reaction mixture is preferably refluxed to promote the reaction.

The reaction time is preferably 10 minutes to 3 days, and more preferably 1 hour to 1 day.

EXAMPLE 1

Synthesis of compound (1)

In 10 mL of toluene, 1.72 g of 4-(9-bromononyloxy) benzoic acid was suspended. To the suspension, 0.71 g of thionyl chloride and a catalytic amount of DMF were added. The mixture was stirred for 1 hour at 40° C. The solvent and the remaining thionyl chloride were distilled away. The residue was dissolved in 10 ml of THF. To the solution, 1.71 g of 4-[4-(octyloxy)benzoyloxy]phenol, 0.78 g of N-ethyldiisopropylamine and a catalytic amount of 4-dimethylaminopyridine were added. The mixture was stirred at room temperature for 3 hours. The reaction mixture was poured into 200 mL of water to form precipitate. The formed precipitate was collected by filtration, washed with water, and recrystallized from isopropyl alcohol to obtain 2.67 g of 4-[4'-(octyloxy)benzoyloxy]phenyl 4-(9-bromononyloxy) benzoate. The obtained 4-[4'-(octyloxy)benzoyloxy]phenyl 4-(9-bromononyloxy)benzoate was dissolved in 20 mL of 2-butanone. To the solution, 0.59 g of 4-dimethylaminopyridine was added. The mixture was stirred under reflux for 3 hours. The reaction mixture was cooled to room temperature. The precipitated crystal was washed with ethyl acetate and acetone to obtain 2.0 g of the compound (1).

$^1$H-NMR (300 MHz, DMSO-d6)δ

0.85 (t, 3H), 1.2–1.4 (m, 20H), 1.75 (m, 6H), 3.20 (s, 6H), 4.10 (t, 4H), 4.15 (t, 2H), 7.05 (d, 2H), 7.15 (m, 4H), 7.35 (s, 4H), 8.10 (m, 4H), 8.30 (d, 2H).

EXAMPLE 2

Synthesis of compound (2)

In 10 mL of toluene, 2.80 g of 4-(9-hydroxynonyloxy) benzoic acid was suspended. To the suspension, 2.97 g of thionyl chloride and a catalytic amount of DMF were added. The mixture was stirred for 1 hour at 100° C. The solvent and the remaining thionyl chloride were distilled away. The residue was dissolved in 10 ml of THF. To the solution, 2.74 g of 4-[4-(octyloxy)benzoyloxy]phenol, 1.29 g of N-ethyl-diisopropylamine and a catalytic amount of 4-dimethylaminopyridine were added. The mixture was stirred at room temperature for 3 hours. The reaction mixture was poured into 200 mL of water to form precipitate. The formed precipitate was collected by filtration, washed with water, and recrystallized from isopropyl alcohol to obtain 4.20 g of 4-[4'-(octyloxy)benzoyloxy]phenyl 4-(9-chlorononyloxy)benzoate. The obtained 4-[4'-(octyloxy)benzoyloxy]phenyl 4-(9-chlorononyloxy)benzoate was dissolved in 20 mL of 2-toluene. To the solution, 1.65 g of 4-dimethylaminopyridine was added. The mixture was stirred at 100° C. for 3 hours. The reaction liquid was cooled to room temperature. The precipitated crystal was washed with ethyl acetate and acetone to obtain 4.52 g of the compound (2).

$^1$H-NMR (300 MHz, DMSO-d$_6$)δ

0.85 (t, 3H), 1.2–1.4 (m, 20H), 1.75 (m, 6H), 3.20 (s, 6H), 4.10 (t, 4H), 4.15 (t, 2H), 7.05 (d, 2H), 7.15 (m, 4H), 7.35 (s, 4H), 8.10 (m, 4H), 8.30 (d, 2H).

EXAMPLE 3

Synthesis of compound (3)

The compound (3) was synthesized by replacing the anion (Cl$^-$) of the compound (2) with F$^-$ in a manner described in J. Org. Chem., (1989), No. 54. pp. 4,827.

EXAMPLE 4

Synthesis of compound (4)

The compound (4) was prepared in the same manner as in Example 1, except that 4-(9-bromononyloxy)benzoic acid was replaced with [4-(9-methanesulfonyloxy)nonyloxy]benzoic acid.

EXAMPLE 5

Synthesis of compound (5)

The compound (5) was prepared in the same manner as in Example 1, except that 4-(9-bromononyloxy)benzoic acid was replaced with [4-(9-toluenesulfonyloxy)nonyloxy]benzoic acid.

EXAMPLE 6

Synthesis of compound (6)

The compound (6) was prepared in the same manner as in Example 1, except that 4-(9-bromononyloxy)benzoic acid was replaced with 4-(2-bromoethoxy)benzoic acid.

EXAMPLE 7

Synthesis of compound (7)

The compound (7) was prepared in the same manner as in Example 1, except that 4-(9-bromononyloxy)benzoic acid was replaced with 4-(2-bromoethoxy)benzoic acid, and 4-[4-(octyloxy)benzoyloxy]phenol was replaced with 3-fluoro-4-[4-(octyloxy)benzoyloxy]phenol.

EXAMPLE 8

Synthesis of compound (8)

The compound (8) was prepared in the same manner as in Example 1, except that 4-(9-bromononyloxy)benzoic acid was replaced with 4-(2-bromoethoxy)benzoic acid, and 4-dimethylaminopyridine was replaced with 4-diethylaminopyridine.

EXAMPLE 9

Synthesis of compound (9)

The compound (9) was prepared in the same manner as in Example 1, except that 4-(9-bromononyloxy)benzoic acid was replaced with 4-(2-bromoethoxy)benzoic acid, and 4-dimethylaminopyridine was replaced with 4-pyrrolidinopyridine.

EXAMPLE 10

Synthesis of compound (10)

In 20 mL of toluene, 3.43 g of 4-(9-bromononyloxy)benzoic acid was suspended. To the suspension, 1.43 g. of thionyl chloride and a catalytic amount of DMF were added. The mixture was stirred for 1 hour at 40° C. The solvent and the remaining thionyl chloride were distilled away. The residue was dissolved in 20 ml of THF. To the solution, 0.44 g of hydroquinone, 1.29 g of N-ethyldiisopropylamine and a catalytic amount of 4-dimethylaminopyridine were added. The mixture was stirred at room temperature for 3 hours. The reaction mixture was poured into 30.0 mL of water to form precipitate. The formed precipitate was collected by filtration, washed with water, and recrystallized from isopropyl alcohol to obtain 2.75 g of 1,4-bis[(9-bromononyloxy)benzoyloxy]benzol. In 10 mL of DMF, 0.76 g of the 1,4-bis[(9-bromononyloxy)benzoyloxy]benzol was dissolved. To the solution, 0.61 g of 4-dimethylaminopyridine was added. The mixture was stirred at 100° C. for 3 hours, and cooled to room temperature. After 50 ml of ethyl acetate was added, precipitated crystal was washed with ethyl acetate to obtain 0.5 g of the compound (10).

$^1$H-NMR (200 MHz, DMSO-d6)δ

1.2–1.4 (m, 20H), 1.75 (m, 8H), 3.20 (s, 12H), 4.10 (t, 4H), 4.15 (t, 4H), 7.05 (d, 4H), 7.10 (d, 4H), 7.35 (s, 4H), 8.10 (d, 4H), 8.30 (d, 4H).

EXAMPLE 11

Synthesis of compound (11)

The compound (11) was prepared in the same manner as in Example 1, except that 4-[4-(octyloxy)benzoyloxy]phenol was replaced with 4-[4-(4-acryloylbutoxy)benzoyloxy]phenol.

EXAMPLE 12

Synthesis of compound (12)

The compound (12) was prepared in the same manner as in Example 1, except that 4-[4-(octyloxy)benzoyloxy]phenol was replaced with 4-[(4-pentylphenyloxy)ethynyl]phenol.

EXAMPLE 13

Synthesis of compound (13)

The compound (13) was prepared in the same manner as in Example 1, except that 4-[4-(octyloxy)benzoyloxy]phenol was replaced with 4-(octyloxy)phenol.

EXAMPLE 14

Synthesis of compound (14)

The compound (14) was prepared in the same manner as in Example 1, except that 4-(9-bromononyloxy)benzoic acid was replaced with 4-(4-bromobutoxy)benzoic acid, and 4-[4-(octyloxy)benzoyloxy]phenol was replaced with 4-(4-cyanophenyl)phenol.

EXAMPLE 15

Synthesis of compound (15)

The compound (15) was prepared in the same manner as in Example 1, except that 4-(9-bromononyloxy)benzoic acid was replaced with 4-(4-bromobutoxy)benzoic acid, and 4-[4-(octyloxy)benzoyloxy]phenol was replaced with 4-(4-methoxyphenyl)phenol.

EXAMPLE 16

Synthesis of compound (16)

The compound (16) was prepared in the same manner as in Example 1, except that 4-(9-bromononyloxy)benzoic acid was replaced with 4-(2-bromoethoxy)benzoic acid, and 4-[4-(octyloxy)benzoyloxy]phenol was replaced with 4-(trans-4-propylcyclohexyl)phenol.

EXAMPLE 17

Synthesis of compound (17)

The compound (17) was prepared in the same manner as in Example 1, except that 4-[4-(octyloxy)benzoyloxy]phenol was replaced with 4-[2-(4-octyloxyphenyl)vinyl]phenol.

EXAMPLE 18

Synthesis of compound (18)

The compound (18) was prepared in the same manner as in Example 1, except that 4-[4-(octyloxy)benzoyloxy]phenol was replaced with 4-[(4-dodecyoxy-benzylidene)amino]phenol.

EXAMPLE 19

Synthesis of compound (19)

The compound (18) was prepared in the same manner as in Example 1, except that 4-[4-(octyloxy)benzoyloxy]phenol was replaced with 4-(4-octyloxyphenyl-azo]phenol.

EXAMPLE 20

Evaluation of Function of Controlling Tilt Angel of Liquid Crystal Molecules A cellulose triacetate film (thickness: 100 μm, size: 270 mm×100 mm, FUJITAC, Fuji Photo Film Co. Ltd.) was used as a support. Polyvinyl alcohol denatured with an alkyl group (MP-203, Kuraray Co., Ltd.) was coated on the support to form a coating layer having a thickness of 0.5 μm. The layer was dried, and subjected to a rubbing treatment.

In 400 weight parts of methyl ethyl ketone, 100 weight parts of the discotic liquid crystal compound (DLC), 1 weight part of a mixture of the fluorine-containing monomers (M-1 and M-2), 10 weight parts of the following polyfunctional monomer (M-3) and the compound (1) were dissolved The prepared solution was coated on the coating layer by using a bar coater, and dried at room temperature. The formed layer was heated at 125° C. to align the liquid crystal molecules. The layer was rapidly cooled to room temperature to fix the alignment. The prepared film was observed to measure an angle giving the minimum retardation. The average tilt angle of the molecules was calculated from the results.

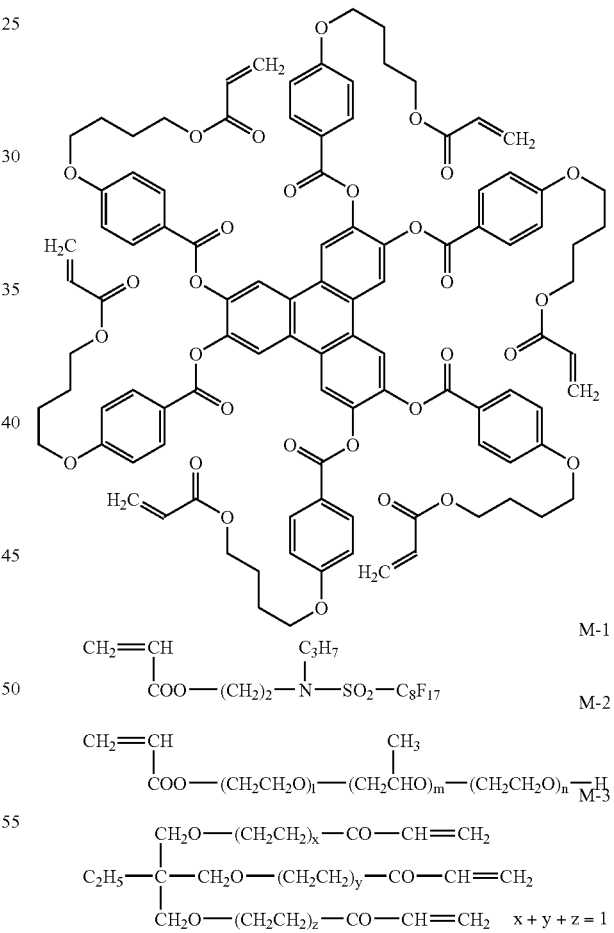

EXAMPLES 21 TO 38 AND COMPARISON EXAMPLES 1 TO 3

The procedure of Example 20 was repeated except that the compound (1) was replaced with the compounds shown in Table 1 to obtain the average tilt angle. The results are set forth in Table 1.

TABLE 1

| Sample No. | Pyridinium compound | Added amount (per liquid crystal) | Average tilt angle |
| --- | --- | --- | --- |
| Example 20 | Compound (1) | 0.01 mol | 37° |
| Example 21 | Compound (2) | 0.01 mol | 38° |
| Example 22 | Compound (3) | 0.01 mol | 37° |
| Example 23 | Compound (4) | 0.01 mol | 36° |
| Example 24 | Compound (5) | 0.01 mol | 35° |
| Example 25 | Compound (6) | 0.01 mol | 37° |
| Example 26 | Compound (7) | 0.01 mol | 37° |
| Example 27 | Compound (8) | 0.01 mol | 36° |
| Example 28 | Compound (9) | 0.01 mol | 36° |
| Example 29 | Compound (10) | 0.01 mol | 37° |
| Example 30 | Compound (11) | 0.01 mol | 37° |
| Example 31 | Compound (12) | 0.01 mol | 36° |
| Example 32 | Compound (13) | 0.01 mol | 35° |
| Example 33 | Compound (14) | 0.01 mol | 37° |
| Example 34 | Compound (15) | 0.01 mol | 37° |
| Example 35 | Compound (16) | 0.01 mol | 36° |
| Example 36 | Compound (17) | 0.01 mol | 35° |
| Example 37 | Compound (18) | 0.01 mol | 36° |
| Example 38 | Compound (19) | 0.01 mol | 36° |
| Comp. Example 1 | None | — | 33° |
| Comp. Example 2 | *Compound (X) | 0.01 mol | 33° |
| Comp. Example 3 | *Compound (X) | 0.30 mol | 37° |

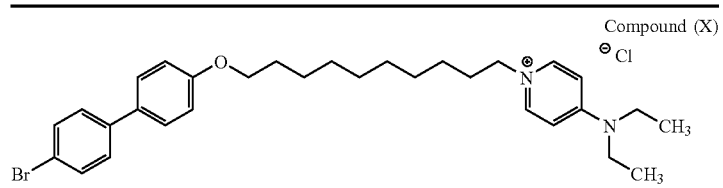

Compound (X)

(corresponding to Compound 3 disclosed in Japanese Patent Provisional Publication No. 2002-37777)

The results of Examples 20 to 38 and Comparison Examples 1 to 3 shown in Table 1 clearly indicate that a small amount of the compound represented by the formula (I) or (II) can increase the tilt angle of liquid crystal molecules.

We claim:

1. A 4-aminopyridinium compound represented by the formula (I):

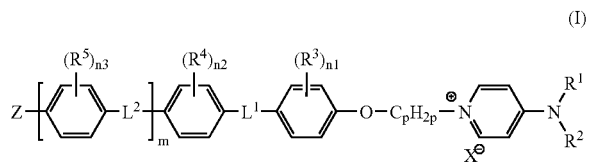

in which $L^1$ is —O—CO—, —CO—O—, —C≡C—, —CH=CH—, —CH=N—, —N=CH— or —N=N—; $L^2$ is a single bond, —O—CO—, —CO—O—, —C≡C—, —CH=CH—, —CH=N—, —N=CH— or —N=N—; m is 0 or 1; p is an integer of 1 to 10; each of $R^1$ and $R^2$ is independently an alkyl group having 1 to 8 carbon atoms, or otherwise $R^1$ and $R^2$ are combined to form a nitrogen-containing saturated ring; Z is cyano, an alkyl group having 1 to 12 carbon atoms, an alkoxy group having 1 to 12 carbon atoms, an acylalkyl group having 3 to 24 carbon atoms, an acyloxyalkyl group having 3 to 24 carbon atoms or an acyloxyalkoxy group having 3 to 24 carbon atoms; each of $R^3$, $R^4$ and $R^5$ is independently a halogen atom; each of n1, n2 and n3 is independently 0 or 1; and X is an anion.

2. The compound as defined in claim 1, wherein $L^1$ in the formula (I) is —O—CO—, —C≡C—, —CH=CH—, —CH=N— or —N=N—.

3. The compound as defined in claim 1, wherein $L^2$ in the formula (I) is a single bond, —CO—O—, —C≡C—, —CH=CH—, —N=CH— or —N=N—.

4. The compound as defined in claim 1, wherein m in the formula (I) is 1.

5. The compound as defined in claim 1, wherein $C_pH_{2p}$ in the formula (I) is an alkylene group of a straight chain represented by $(CH_2)_p$.

6. The compound as defined in claim 1, wherein each of $R^1$ and $R^2$ in the formula (I) is independently an alkyl group having 1 to 6 carbon atoms.

7. The compound as defined in claim 1, wherein each of n1, n2 and n3 in the formula (I) is 0.

8. The compound as defined in claim 4, wherein Z in the formula (I) is cyano, an alkyl group having 1 to 10 carbon atoms or an alkoxy group having 1 to 10 carbon atoms.

9. The compound as defined in claim 1, wherein m in the formula (I) is 0, and Z in the formula (I) is an alkyl group having 7 to 12 carbon atoms, an alkoxy group having 7 to 12 carbon atoms, an acylalkyl group having 7 to 12 carbon atoms, an acylalkoxy group having 7 to 12 carbon atoms, an acyloxyalkyl group having 7 to 12 carbon atoms or an acyloxyalkoxy group having 7 to 12 carbon atoms.

10. The compound as defined in claim 1, wherein X in the formula (I) is a halide ion or a sulfonate ion.

11. A 4-aminopyridinium compound represented by the formula (II):

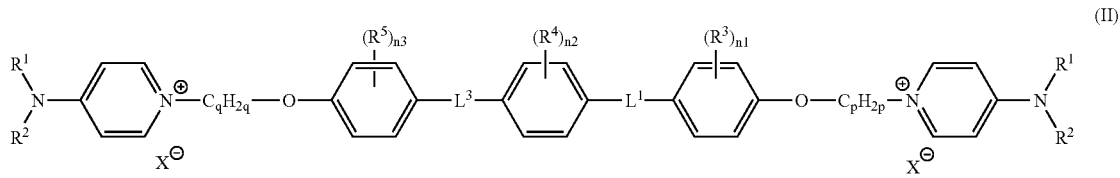

in which each of L¹ and L³ is independently —O—CO—, —CO—O—, —C≡C—, —CH=CH—, —CH=N—, —N=CH— or —N=N—; each of p and q is independently an integer of 1 to 10; each of R¹ and R² is independently an alkyl group having 1 to 8 carbon atoms, or otherwise R¹ and R² are combined to form a nitrogen-containing saturated ring; each of R³, R⁴ and R⁵ is independently a halogen atom; each of n1, n2 and n3 is independently 0 or 1; and X is an anion.

12. The compound as defined in claim 11, wherein L¹ in the formula (II) is —O—CO—, —C≡C—, —CH=CH—, —CH=N— or —N=N—.

13. The compound as defined in claim 11, wherein L³ in the formula (II) is —CO—O—, —C≡C—, —CH=CH—, —N=CH— or —N=N—.

14. The compound as defined in claim 11, wherein $C_pH_{2p}$ in the formula (II) is independently an alkylene group of a straight chain represented by $(CH_2)_p$.

15. The compound as defined in claim 11, wherein $C_qH_{2q}$ in the formula (II) is independently an alkylene group of a straight chain represented by $(CH_2)_q$.

16. The compound as defined in claim 11, wherein each of R¹ and R² in the formula (II) is independently an alkyl group having 1 to 6 carbon atoms.

17. The compound as defined in claim 11, wherein each of n1, n2 and n3 in the formula (II) is 0.

18. The compound as defined in claim 11, wherein X in the formula (II) is a halide ion or a sulfonate ion.

* * * * *